United States Patent [19]

Gaffar

[11] 4,143,126
[45] Mar. 6, 1979

[54] DENTAL PROPHYLACTIC PASTE

[75] Inventor: Maria C. Gaffar, Somerset, N.J.

[73] Assignee: Colgate Palmolive Company, New York, N.Y.

[21] Appl. No.: 812,030

[22] Filed: Jul. 1, 1977

[51] Int. Cl.$^2$ .......................... A61K 7/16; A61K 7/18
[52] U.S. Cl. .......................................... 424/49; 424/52; 424/57
[58] Field of Search .................................... 424/49–58

[56] References Cited

U.S. PATENT DOCUMENTS

| | | | |
|---|---|---|---|
| 1,275,275 | 8/1918 | Levinson | 424/55 X |
| 1,304,600 | 5/1919 | Pond | 424/360 |
| 1,445,351 | 2/1923 | Pfanstiehl | 424/55 |
| 1,536,305 | 5/1925 | Nitardy | 424/58 X |
| 2,025,655 | 12/1935 | Faunce | 424/58 X |
| 2,059,396 | 11/1936 | Ripert | 424/58 X |
| 2,154,168 | 4/1939 | Klein et al. | 424/57 X |
| 2,218,172 | 10/1940 | Kokatnur | 424/53 X |
| 3,257,282 | 6/1966 | Muhler | 424/52 |
| 3,337,412 | 8/1967 | Elbreder | 424/151 X |
| 3,892,843 | 7/1975 | Muhler et al. | 424/52 |

OTHER PUBLICATIONS

Dentitricus–1970, pp. 142–145, "Dentifrices for Dentists", Jefopoulos, Noyes Data Corp., Park Ridge, N.J.
Braden et al., J. Dental Research 55(3):353–356, May, Jun. 1976, "Rheology of Fluoride Gels".

*Primary Examiner*—Shep K. Rose
*Attorney, Agent, or Firm*—Robert L. Stone; Murray M. Grill; Herbert S. Sylvester

[57] ABSTRACT

A dental prophylactic paste comprising an abrasive, a humectant, gelatin and optional flavoring and preservative ingredients which possesses improved flowability by which the paste can be poured through a nozzle under low pressure into individual containers as well as improved non-spatterability and cleaning efficiency in use by the dentist.

6 Claims, No Drawings

DENTAL PROPHYLACTIC PASTE

This invention relates to prophylactic dental pastes used by dentists in the periodic cleaning of teeth.

It is an object of the invention to provide a prophylactic dental paste with good flowability properties so that the same can be poured into individual containers through a nozzle with a minimum of pressure.

Another object of the invention is to provide a prophylactic dental paste which is substantially non-spattering in use.

Yet another object of the invention is to provide a prophylactic dental paste with improved cleaning efficiency.

The foregoing objects are accomplished by providing a composition an abrasive, a humectant and gelatin with optional ingredients such as flavoring agents, preservatives and the like.

The closest prior art known to applicant is the Najjar U.S. Pat. No. 3,228,845. This patent discloses a prophylactic dental paste which combines about 50% pumice flour, about 20-25% glycerine, about 12% water, up to about 2% agar-agar and up to about 10% sodium silicate which Najjar asserts is non-splattering and flows evenly and smoothly under pressure. A commercial preparation is marketed as Nupro by Janar Company of Grand Rapids, Mich. under said patent.

Applicant has discovered that by using gelatin instead of agar-agar in a range by weight of about 0.01 to 10%, preferably about 1-5%, and abrasives in a range by weight of about 40-60%, preferably about 40-50%, the characteristics of flowability, non-spatterability, and cleaning efficiency are improved over the paste disclosed in and sold commercially under the Najjar patent.

The gelatin which is employed in the instant prophylactic dental paste may be Type A having a gel strength of 75-350 Bloom gms. or Type B having a gel strength of 75-250 Bloom gms. as described in the publication "Gelatin" prepared and published by the Gelatin Manufacturers Institute of America, Inc., 516 Fifth Ave., New York, N.Y., copyright 1973, which is herein incorporated by reference.

Although the preferred abrasive is medium grade pumice, other abrasives can be used such as hard minerals (Mohs hardness of 5 to 9), for example, silica, silicates such as calcium silicate, zirconium silicate, topaz, feldspar, talcs, alumina, titanium dioxide and ferric titanate, etc., and softer minerals (Mohs hardness below 5), for example, the phosphates such as $CaHPO_4$, $CaHPO_2 \cdot 2H_2O$, $Ca_2P_2O_7$, $Ca_3(PO_4)_2$, and sodium metaphosphate as well as gypsum, apatite, calcite, etc.

The prophylactic dental paste also includes a humectant and, while the preferred humectant in the instant composition is glycerin, other glycols may be used as well, such as ethylene glycol, propylene glycol and the like. In those pastes which contain water, the humectant content can be about 15-45% by weight, preferably 20-35%.

Additionally, the paste may be formulated with silica gel or with silicates such as alkali metal and ammonium silicates, preferably sodium metasilicate, and may also include the fluoride ion and, while the preferred fluoride compound is ammonium silicofluoride, other fluorides or fluoride-containing substances may be used such as $Na_2FPO_4$, $NaF$, $KF$, $LiF$, $SnF_2$, $SnF_4$, $SnZnF_6$, $TeF_2$, $Na_2SiF_6$, fluorozirconates, fluorostannites, fluoroborates, etc.

The instant composition may also be formulated to combine a mineral abrasive, a humectant, gelatin, a silicate and an acid anhydride to form a water-free flowable paste. While the preferred silicate is sodium metasilicate, other soluble silicates may also be used such as potassium metasilicate, sodium or potassium orthosilicates, disilicates, polysilicates, quaternary ammonium silicates, etc. Also, while succinic anhydride is preferred, other acid anhydrides which can be used are acetic, maleic, fumaric, etc.

The following are non-limitative examples of the instant prophylactic dental pastes.

EXAMPLE 1

| | % (W/W) |
|---|---|
| Pumice, medium (abrasive) | 50.00 |
| Gelatin, Type A, 300 Bloom gms. | 2.00 |
| Glycerin (humectant) | 36.00 |
| Water | 9.43 |
| Flavor | 0.50 |
| Sweetener (e.g. sorbitol) | 2.00 |
| Color | 0.02 |
| Sodium benzoate (preservative) | 0.05 |
| | 100.00 |

The abrasive, flavor, sweetener, color and preservative are placed in a mixer bowl. The humectant is added and the ingredients mixed well. The gelatin is added to hot water and stirred until it is dissolved. While still hot, the aqueous gelatin solution is added gradually to the ingredients in the mixer bowl and mixed for about 10 minutes. The paste is warmed to 30-40° C. and pumped by a nozzle under relatively low pressure into individual containers.

EXAMPLE 2

| | % (W/W) |
|---|---|
| Pumice, medium | 40.00 |
| Gelatin, Type A, 300 bloom gms. | 2.00 |
| Glycerin | 42.48 |
| Sodium metasilicate | 2.00 |
| Sweetener (sorbitol) | 2.00 |
| Flavor | 0.50 |
| Color | 0.02 |
| Water | 10.95 |
| Sodium benzoate | 0.05 |
| | 100.:0 |

The gelatin is added to hot water and stirred until dissolved. The sodium metasilicate is dissolved in the glycerin with warming. The pumice, sweetener, flavor, color and sodium benzoate are mixed and to this mixture is added the metasilicate-glycerin solution and again mixed, after which the hot aqueous gelatin solution is added and mixed well for about 10 minutes. The paste is now ready to be pumped by nozzle under relatively low pressure into individual containers at 30-40° C. In this paste the preferred range of silicates is about 1-10% by weight and that of the gelatin about 1-5% by weight.

EXAMPLE 3

| | % (W/W) |
|---|---|
| Pumice, medium | 50.00 |
| Gelatin, Type A, 300 Bloom gms. | 2.00 |
| Glycerin | 30.00 |
| Silica gel | 2.00 |

-continued

| | % (W/W) |
|---|---|
| Sweetener (sorbitol) | 2.00 |
| Flavor | 0.50 |
| Color | 0.02 |
| Water | 13.43 |
| Sodium benzoate | 0.05 |
| | 100.00 |

The silica gel used herein is Syloid 244 made by the Grace Chemical Co. and ranges in particle size from 1–30 microns. The method of preparing the paste for this formulation is the same as that in Example 2 except that silica gel replaces the sodium metasilicate. Here again, the preferred range in this type of paste of silica gel is about 1–10% by weight and that of gelatin about 1–5% by weight.

EXAMPLE 4

| | % (W/W) |
|---|---|
| Purified water | 27.93841 |
| Potassium sorbate | 0.00700 |
| Sorbitol | 2.00000 |
| Ammonium silicofluoride | 1.88000 |
| Sodium biphosphate, N.F. | 0.16284 |
| Color | 0.02500 |
| Phosphoric acid, 85%, N.F. | 0.18675 |
| Glycerin, 99.5% | 3.30000 |
| Flavor | 0.50000 |
| Silica Ottawa 295 (abrasive) | 60.00000 |
| Gelatin, Type A, 300 Bloom gms. | 2.00000 |
| Silica gel (Syloid 244) | 2.00000 |
| | 100.00000 |

The gelatin and color are dissolved in 10 ml. water. The potassium sorbate, sorbitol, sodium biphosphate and ammonium silicofluoride are dissolved in water at 50° C. with stirring in a mixer bowl. The phosphoric acid and glycerin are then added and mixed for about 5 minutes and then the aqueous color and gelatin solution are added to the mixer bowl. The pH of the mixture is between 2.8 and 3.4. The flavor is then added and mixed well for about 10 minutes. Sift the Ottawa silica #295 and add it to the mixer bowl and mix for about 10 minutes. Warm the mixture if it gets too thick. Transfer to individual containers as described hereinbefore. The preferred $F^-$ content is about 0.1–5.0% and that of the gelatin is 1–5% by weight.

EXAMPLE 5

| | % (W/W) |
|---|---|
| Pumice, medium | 45.00 |
| Gelatin, Type A, 300 Bloom gms. | 2.00 |
| Glycerin | 40.81 |
| Sodium metasilicate . 9 H$_2$O | 6.50 |
| Succinic anhydride | 3.12 |
| Color | 0.02 |
| Sweetener (sorbitol) | 2.00 |
| Flavor | 0.50 |
| Sodium benzoate | 0.05 |
| | 100.00 |

The sodium metasilicate is dissolved in 15 g. of glycerin with warming and then allowed to cool to room temperature. The succinic anhydride is dissolved in the rest of the glycerin with heating at about 65° C. and then allowed to cool to room temperature. The pumice, color, sweetener and flavor are combined in a mixer bowl and mixed well for about 5 minutes. The sodium metasilicate-glycerin and succinic anhydride-glycerin solutions are combined and then added to the mixture in the mixer bowl where the ingredients are mixed for about 10 minutes to obtain a homogeneous mass after which it is pumped into individual containers as described hereinbefore.

This paste composition must be kept as free of water as possible so as not to hydrolyze the anhydride and produce the acid, which would cause the paste to harden too quickly and impair its flowability. In this paste composition the preferred range of silicates is about 1–12% by weight and that of the acid anhydride about 1–10% by weight.

Regarding the important property of flowability (viscosity) which determines the ease with which the paste can be pumped through a nozzle with very low pressure into individual containers to form discs, capsules and the like, a comparison was made between the instant paste composition containing gelatin with a similar agar-agar containing composition as in the Najjar patent. The following tables show the compositions compared and the viscosity results.

Table I

| Paste Composition | Agar-Agar | Gelatin |
|---|---|---|
| Pumice, medium | 40% | 40% |
| Glycerol | 28% | 28% |
| Water | 26% | 26% |
| Sodium metasilicate | 5% | 5% |
| Agar-agar | 5% | — |
| Gelatin, Type A, 300 Bloom gms. | — | 5% |
| Viscosity (cps) bet. 30–40° C | 4800 | 1400 |

The viscosity of the paste was measured at 30–40° C. using a Brookfield Viscosimeter (Spindle LV#4, Speed-30).

Manifestly, the agar-agar-containing paste is less flowable than the gelatine-containing paste.

Table II

| Paste Composition | Agar-Agar | Gelatin |
|---|---|---|
| Pumice, medium | 40% | 40% |
| Glycerol | 28% | 28% |
| Water | 26% | 27% |
| Sodium metasilicate | 5% | 3% |
| Agar-Agar | 1% | — |
| Gelatin, Type A, 300 Bloom gms. | — | 2% |
| Viscosity (cps) bet. 30–40° C | 4800 | 1200 |

Manifestly, the agar-agar-containing paste is less flowable than the gelatine-containing paste. In this Table the agar-agar and gelatin-containing pastes are comparable. The water content was increased by 1% in the gelatin-containing paste to allow for complete solution of the gelatin. The silicate content was reduced by 2% in the gelatin-containing paste to reduce the alkalinity which denatures gelatin. Thus, even with the use of twice as much by weight of gelatin as agar-agar in the paste, there is a substantial difference in the viscosity, yet at room temperature the gelatin-containing paste of the instant invention has a good solid consistency readily and easily applicable by a dentist to the teeth in the cleaning process.

Two additional comparisons were made between the instant gelatin-containing paste and the Najjar agar-agar-containing paste commercially available for various grades as Nupro.

For these comparisons, in vitro procedures were developed.

A desirable property of a dental prophylactic paste is its ability to adhere to the prophylaxis cup under prophy conditions. This property not only makes the paste economical to use but, by reducing spattering, minimizes soiling of the dental handpiece, the office and the clothing of the dentist and patient. To test this spattering property the following in vitro test was developed.

Extracted human incisors were cleaned, sliced and embedded onto epoxy so that only the enamel surfaces were shown. A conventional webbed rubber prophylaxis cup was weighed empty in a sensitive microbalance. The cup was attached to a 1500 rpm constant speed motor and was dipped into the paste for 10 seconds. The cup was then removed, excess paste outside its rim wiped off and the filled cup was reweighed. The filled cup was then reattached to the motor and caused to come into contact with the tooth enamel surface at a constant load of 250 gm. for 60 seconds. The cup was again removed from the motor, any paste on the outside wiped off, and the cup was reweighed. The percentage of paste lost in 60 seconds was calculated from the following formula.

$$\% \text{ Paste Loss} = \frac{\text{Amt. of paste in filled cup} - \text{Amt. of paste after 60 sec.}}{\text{Amt. of paste in filled cup}} \times 100$$

The following Table shows the comparative results obtained:

Table III

| Paste | % Paste Loss (60 sec.) |
|---|---|
| Agar-agar silicate paste (Nupro) | 10.5 |
| Gelatin paste (Example 1) | 7.0 |
| Gelatin-silica gel paste (Example 3) | 6.5 |

Thus, the instant gelatin-containing paste possesses reduced spattering properties.

The in vitro cleaning efficiency test was carried out as follows. The reflectance readings of the enamel surfaces shown of the sliced teeth were made by means of a Gardner Reflectance instrument. A concentrated coffee solution was mixed with diluted egg albumin (2 ml. egg albumin:5 ml. water) in a ratio of 1:2. A few drops of this mixture was spread evenly on each tooth enamel slice (prepared as described hereinbefore) and allowed to dry. The stained tooth slice was then covered with a thin coat of Epon Resin 815, made by Miller Stephenson Chemical Co. of Danbury, Conn., and allowed to dry. The primer for this resin is diethylenetriamine (1:10 ratio). The resin when allowed to dry over the coffee-albumin stain produces a tenacious stain which can only be removed under dental prophylaxis conditions similar to in vivo stains.

The webbed rubber prophylaxis cup was mounted on the 1500 rpm constant speed motor and dipped into the prophy paste for 10 seconds. The stained tooth embedded in a holder was placed on top of a one-armed platform balance directly below the paste-filled cup. The balance was then raised to make contact between the tooth slice and the cup and a 250 gm. load was applied with the balance counter-weights. The motor was turned on and the paste-filled cup at 1500 rpm was allowed to work on the stained tooth surface for 60 seconds after which the motor was stopped, the tooth slice rinsed under running deionized water and allowed to dry. The amount of stain left on the tooth surface was then measured using the Gardner Reflectance instrument which measures reflectance of light from the tooth surface and the intensity of the color on the tooth surface in R.V. (reflectance value) units, and the percentage of stain removed was calculated, as follows:

$$\% \text{ Stain Removed} = \frac{(R.V. \text{ after 60 sec. cleaning} - R.V. \text{ cleaning}) - (R.V. \text{ before staining} - R.V. \text{ before cleaning})}{R.V. \text{ before staining} - R.V. \text{ before cleaning}} \times 100$$

The higher the percentage removal, the better the cleaning ability of the paste.

The comparative results obtained are shown in the following Table:

Table IV

| Paste | % Stain Removed (60 sec.) |
|---|---|
| Agar-Agar silicate (Nupro) | 31 |
| Gelatin paste (Example 1) | 74 |
| Gelatin-Silica gel paste (Example 3) | 41 |

Thus, the instant dental prophylactic paste is of such composition that its superior flowability allows it to be poured through a nozzle under low pressure into individual containers wherein it forms solid discs or capsules at room temperature and which when applied to teeth by means of the cup mounted on a conventional motor driven dental tool will accomplish improved cleaning with a minimum, if any, spattering.

What is claimed is:

1. A fluoride-free dental prophylactic paste which is substantially non-spattering and has improved flowability through a nozzle under low pressure comprising a pumice abrasive, a humectant and gelatin, the abrasive being present in an amount by weight of about 40–60% and the gelatin being present in an amount by weight of about 0.01 to 10.0% which is sufficient to impart to said composition a viscosity of between 1200 and 1400 centipoises at a temperature between 30° and 40° C.

2. The dental prophylactic paste of claim 1 wherein the abrasive content is about 40–50% and the gelatin content is about 1–5%.

3. The dental prophylactic paste of claim 1 wherein and the humectant is glycerol.

4. The dental prophylactic paste of claim 1 and an alkali metal silicate in an amount of about 1–10% by weight.

5. The dental prophylactic paste of claim 1 and silica gel in an amount of about 1–10% by weight.

6. The dental prophylactic paste of claim 1, a silicate in the amount of about 1–12% by weight and an acid anhydride in an amount of about 1–10% by weight.

* * * * *